United States Patent [19]

Anderson et al.

[11] Patent Number: 5,079,343

[45] Date of Patent: Jan. 7, 1992

[54] INTRACELLULAR ANTIGEN FOUND IN SUBPOPULATION OF CD8+ T LYMPHOCYTES AND MONOCLONAL ANTIBODY REACTIVE WITH SAME

[75] Inventors: Paul J. Anderson, Watertown; Michel Streuli, Somerville; Stuart F. Schlossman, Newton Centre, all of Mass.

[73] Assignee: Dana-Farber Cancer Institute, Inc., Boston, Mass.

[21] Appl. No.: 460,678

[22] Filed: Jan. 5, 1990

[51] Int. Cl.[5] .................... A61K 43/00; A61K 39/00; C12Q 1/68; C07K 3/00
[52] U.S. Cl. .................... 530/387; 424/1.1; 424/85.8; 435/6; 530/402
[58] Field of Search .................... 435/6; 530/402, 587, 530/1.1; 424/85.8

[56] References Cited

U.S. PATENT DOCUMENTS 4,925,648  5/1990  Hansen et al. .................... 530/402

OTHER PUBLICATIONS

Anderson et al., "A Monoclonal Antibody Reactive with a 15-kDa Cytoplasmi8c Granule-Associated Protein Defines a Subpopulation of CD8+ T Lymphocytes[1]," J. of Immunology, 144:574-582 (1990).
Meuer et al., "Clonal Analysis of Human Cytotoxic T Lymphocytes: T4+ and T8+ Effector T Cells Recognize Products of Different Major Histocompatibility Complex Regions," Proc. Natl. Acad. Sci. U.S.A., 79:4395-4399.
Reinherz et al., "The Human T Cell Receptor: Analysis with Cytotoxic T Cell Clones," Immunological Rev., 74:83-112 (1983).
Podack et al., "Cytolytic T Cell Granules Isolation, Structural, Biochemical, and Functional Characterization," J. Exp. Med., 160:695-710 (1984).
Podack et al., "Isolation and Biochemical and Functional Characterization of Perforin 1 from Cytolytic T-Cell Granules," Proc. Natl. Acad. Sci. U.S.A., 82:8629-8633 (1985).
Shinkai et al., "Homology of Perforin to the Ninth Component of Complement (C9)," Nature, 334:525-527 (1988).
Lowrey et al., "Cloning, Analysis, and Expression of Murine Perforin 1 cDNA, a Component of Cytolytic T-Cell Granules with Homology to Complement Component C9," Proc. Natl. Acad Sci. U.S.A., 86:247-251 (1989).
Pasternack et al., "A Novel Serine Esterase Expressed by Cytotoxic T Lymphocytes," Nature, 314:743-745 (1985).
Pasternack et al., "Serine Esterase in Cytolytic T Lymphocytes," Nature, 322:740-743 (1986).
Young et al., "Isolation and Characterization of a Serine Esterase from Cytolytic T Cell Granules," Cell, 47:183-194 (1986).
Schmidt et al., "T11/CD2 Activation of Cloned Human Natural Killer Cells Results in Increased Conjugate Formation and Exocytosis of Cytolytic Granules," J. of Immunology, 142:991-1002 (1988).
Kamada et al., "Indentification of Carboxypeptidase and Tryptic Esterase Activities that are Complexed to Proteoglycans in the Secretory Granules of Human Cloned Natural Killer Cells[1]," J. of Immunology, 142:609-615 (1989).

(List continued on next page.)

*Primary Examiner*—Robert A. Wax
*Assistant Examiner*—Bradley L. Sisson
*Attorney, Agent, or Firm*—Fish & Richardson

[57] ABSTRACT

A 15 kd protein antigen is associated with cytoplasmic granules in cytolytic T lymphocytes and natural killer cells. Monoclonal antibodies immunologically reactive with the 15 kd protein and nucleic acid probes encoding polypeptides that are immunologically cross-reactive with the 15 kd protein can be used, e.g., to identify cytolytic lymphocytes in a sample. Cloned cDNA encoding the antigen can be used to produce the antigen.

2 Claims, 1 Drawing Sheet

OTHER PUBLICATIONS

Takayama et al., "Antigen Receptor-Triggered Secretion of a Trypsin-Type Esterase from Cytotoxic T Lymphocytes," J. of Immunology 138:566–569 (1987).

Schmidt et al., "Specific Release of Proteoglycans from Human Natural Killer Cells During Target Lysis," Nature, 318:289–291 (1985).

Kriegler et al., "A Novel Form of TNF/Cachectin is a Cell Surface Cytotoxic Transmembrane Protein: Ramifications for the Complex Physiology of TNF," Cell, 53:45–53 (1988).

Yamamoto et al., "Indentification of LT and TNF-like" LT forms from Stimulated Natural Killers, Specific and Nonspecific Cytotoxic Human T Cells in vitro[1], J. of Immunology, 137:1878–1884 (1986).

Fiskum et al., "The Cytoskeleton of Digitonin-Treated Rat Hepatocytes," Proc. Natl. Acad. Sci. U.S.A., 77:3430–3434 (1980).

Anderson et al., "Monoclonal Antibodies Reactive with the T Cell Receptor Chain: Production and Characterization Using a New Method," J. of Immunology, 143:1899–1904 (1989).

```
GGT ACC AAA CAG CTA TCA TAT GAT GAG GTT GTA AAT CAG TCT AGT

CCA AGC AAC TGT ACT GTA TAC TGT GGA GGT GTT ACT TCT GGG CTA

ACA GAA CAA CTA ATG CGT CAG ACT TTT TCA CCA TTT GGA CAA ATA

M   E   I   R   V   F   P   D   K   G   Y   S   F   V   R
ATG GAA ATT CGA GTC TTT CCA GAT AAA GGA TAT TCA TTT GTT CGG

F   N   S   H   E   S   A   A   H   A   I   V   S   V   N
TTC AAT TCC CAT GAA AGT GCA GCA CAT GCA ATT GTT TCT GTT AAT

G   T   T   I   E   G   H   V   V   K   C   Y   W   G   K
GGT ACT ACC ATT GAA GGT CAT GTT GTG AAA TGC TAT TGG GGC AAA

E   T   L   D   M   I   N   P   V   S   T   A   E   S   I
GAA ACT CTT GAT ATG ATA AAT CCC GTG CAA CAG CAG AAT CAA ATT

G   Y   P   Q   P   Y   G   Q   W   G   Q   W   Y   G   N
GGA TAT CCC CAA CCT TAT GGC CAG TGG GGC CAG TGG TAT GGA AAT

A   Q   Q   I   G   Q   Y   M   P   N   G   W   Q   V   P
GCA CAA CAA ATT GGC CAG TAT ATG CCT AAT GGT TGG CAA GTT CCT

A   Y   G   M   Y   G   Q   A   W   N   Q   Q   G   F   N
GCA TAT GGA ATG TAT GGC CAG GCA TGG AAC CAG CAA GGA TTT AAT

Q   T   Q   S   S   A   P   W   M   G   P   N   Y   G   V
CAG ACA CAG TCT TCT GCA CCA TGG ATG GGA CCA AAT TAT GGA GTG

Q   P   P   Q   G   Q   N   G   S   M   L   P   N   Q   P
CAA CCG CCT CAA GGG CAA AAT GGC AGC ATG TTG CCC AAT CAG CCT

S   G   Y   R   V   A   G   Y   E   T   Q
TCT GGG TAT CGA GTG GCA GGG TAT GAA ACC CAG TGA ATA AGG ACT

CCA GAA TCT AAA GCC AGT GGC TTG AGG CTA CAG GGA GTG TAG TAA...
```

FIGURE

INTRACELLULAR ANTIGEN FOUND IN SUBPOPULATION OF CD8+ T LYMPHOCYTES AND MONOCLONAL ANTIBODY REACTIVE WITH SAME

BACKGROUND OF THE INVENTION

The invention was made in the course of an award or grant from the Arthritis Foundation and the National Institutes of Health, and the United States government, therefore, has rights in this invention.

This invention relates to monoclonal antibodies and related antigens, and specifically to monoclonal antibodies to intracellular antigens in lymphocytes.

Monoclonal antibodies reactive with T cell surface molecules have been instrumental in defining phenotypic and functional heterogeneity in peripheral blood lymphocyte populations. The surface markers designated CD4 and CD8 have been shown to define cells possessing helper/inducer and cytotoxic/suppressor functions, respectively. Both CD4+ and CD8+ lymphocytes express intracellular effector molecules that are released in response to specific activating stimuli. In CD4+ helper cells, these effectors are lymphokines such as IL-2, IL-4 and IFN-γ. Although CD8+ cytolytic cells can also produce lymphokines, they are characterized by their inclusion of cytoplasmic granules containing putative cytolytic effector molecules such as perforin, serine proteases, and proteoglycans. Target cell recognition is accompanied by the secretion of these intracellular effectors.

SUMMARY OF THE INVENTION

In general, one aspect of the invention features a monoclonal antibody (preferably of class IgG) which antibody is immunologically reactive with a 15 kd protein associated with cytoplasmic granules in cytolytic T lymphocytes and natural killer cells. The phrase "immunologically reactive" means that the antibody and antigen bind with sufficient specificity to permit immunoassay of the antigen or antibody. The phrase does not necessarily exclude the possibility that the antibody binds other antigens, e.g., multimers of the antigen or related proteins as described below.

Other aspects of the invention feature the 15 kd protein, engineered nucleic acid encoding a polypeptide composed of a sequence of amino acids that is immunologically cross-reactive with the 15 kd protein, and a method of producing the polypeptide by expressing the engineered nucleic acid. The phrase "immunologically cross-reactive" means that the polypeptide encoded by the engineered nucleic acid binds specifically to the same antibody that is immunologically reactive with the 15 kd protein.

In preferred embodiments, the antibody is monoclonal antibody TIA-1, the protein is found in a subpopulation of CD8+ T lymphocytes from peripheral blood mononuclear cells, and the nucleic acid substantially corresponds to nucleic acid deposited in the ATCC as strain number ATCC 68202.

Since the 15 kd protein is specifically characteristic of cytolytic lymphocytes, another aspect of the invention features methods of identifying cytolytic lymphocytes in a sample (e.g., a sample comprising populations of peripheral blood mononuclear cells) which involve contacting the sample with a monoclonal antibody described above or with a nucleic acid probe having a nucleic acid sequence (e.g., at least six nucleotides long) which specifically hybridizes under hybridizing conditions to DNA encoding the 15 kd protein described above, and determining binding of the antibody or nucleic acid probe.

In another aspect, the invention features methods of determining the extent of T cell infiltration into a specific tissue of a patient which involve contacting a fixed tissue section from the specific tissue of the patient with any one of the antibodies or nucleic acid probes described above, and determining the binding of the antibody or nucleic acid probe to the fixed tissue section.

The ability to monitor the presence of cytolytic lymphocytes through antibody binding will provide an early warning of the presence of an infective agent, such as the HIV virus, in a patient. cDNA probes capable of detecting nucleic acid encoding the novel effector protein, TIA antigen, provide an especially sensitive means of detecting the early presence of such agents.

Other features and advantages of the invention will be apparent from the following description of the preferred embodiments thereof, and from the claims.

BRIEF DESCRIPTION OF THE DRAWING

The FIGURE represents the nucleotide sequence of cDNA encoding TIA-1 antigen and predicted amino acid sequence of the antigen, the cDNA being deposited in the ATCC as strain number ATCC 68202.

DESCRIPTION OF THE PREFERRED EMBODIMENTS

Monoclonal antibody TIA-1, selected as differentiating between permeabilized and unpermeabilized T cells, recognizes a 15 kd, intracellular protein, the TIA-1 antigen, which is found in a subpopulation of CD8+ lymphocytes from peripheral blood mononuclear cells and in natural killer cells. TIA-1 antigen is observed by immunoelectron microscopy to be associated with the membrane of cytoplasmic granules in cytolytic T lymphocytes.

Method of isolation of TIA-1

Hybridomas suitable to be screened for production of antibodies reactive with intracellular antigens were prepared by immunizing 6-week-old Balb/c mice with permeabilized T lymphocytes (25–30×10$^6$) at 21 day intervals over a 9–12 week period. The immunogen was prepared using Ficoll purified peripheral blood mononuclear cells obtained from plateletpheresis residues that were rosetted with sheep erythrocytes (Lay et al., Nature 300:267, 1971). Purified T lymphocytes were washed three times in PBS, resuspended at 5×10$^6$ cells/ml and permeabilized by the addition of digitonin (10 μg/ml) for 5 minutes on ice. The adequacy of permeabilization was monitored by determining trypan blue uptake, which was typically greater than 90%. Permeabilized lymphocytes were pelleted, resuspended at 25–30×10$^6$ cells/ml in sterile PBS and injected intraperitoneally into Balb/c mice. Splenocytes from immunized mice were fused to NS-1 myeloma cells for the production of hybridomas (Kohler et al., Nature 256:495, 1975).

Individual clones of the hybridomas as prepared above were screened for reactivity to permeabilized T lymphocytes by a modification of the flow cytometric method. In order to permeabilize the cells without causing undue cellular damage or the excessive loss of intracellular constituents and in order to protect the permeabilized cells against disintegration during the many washes required in preparation for flow cytometric analysis, T lymphocytes purified by sheep erythrocyte rosetting were first stabilized by mild fixation with 0.01% formaldehyde in PBS for 20 minutes on ice. Cells were then washed four times with ice cold PBS, resuspended at $5 \times 10^6$ cells/ml in PBS and permeabilized by the addition of digitonin (10 μg/ml) for 5 minutes on ice. After the adequacy of permeabilization had been confirmed by trypan uptake, cells were pelleted and resuspended in PBS at $20 \times 10^6$ cells/ml. Hybridoma supernatants were added to permeabilized cells in a 1:1 ratio. After 30 minutes on ice, cells were washed three times with PBS containing 0.05% Tween-20 to remove unbound antibody, further incubated with goat anti-mouse-FITC, washed, resuspended in PBS and 1% formaldehyde, and analyzed flow cytometrically, using an Epics 752 flow cytometer.

Specificity of expression of TIA-1 antigen

Activated T lymphocytes can contain CD4 or CD8 among other cell surface proteins. Purified populations of CD4+ and CD8+ lymphocytes were found to contain the TIA-1 antigen preferentially in the CD8+ subset. On average, in an antibody binding assay of permeabilized cells, TIA-1 stained $6\pm 2\%$ of CD4+ cells and $55\pm 7\%$ of CD8+ cells. TIA-1 antigen is also expressed in natural killer (NK) cell clones, but not in immortalized T cell lines (Jurkat, HPB-ALL, CEM, HUTL-78), nor in B cell lines (Daudi, BJAB, Raji). (See Table below).

TABLE

Flow cytometric analysis of TIA-1 antigen expression in permeabilized hematopoetic cells.

| Cell Type | Relative Expression |
| --- | --- |
| B cells | − |
| T cells | + |
| CD4+ T cells | +/− |
| CD8+ T cells | +++ |
| Thymocytes | − |
| Con A activated thymocytes | + |
| JJ1 (NK clone) | +++ |
| CNK6 (NK clone) | +++ |
| JT$_\beta$18 (NK clone) | +++ |
| YT (NK cell leukemia) | + |
| T4T8Cl (CD4+, CD8+ clone) | +++ |
| A2p (CD8+ cell line) | ++ |
| M (CD4+ clone) | + |
| MM (CD4+ clone) | + |
| N (CD4+ clone) | +/− |
| P (CD4+ clone) | + |

Effect of T cell activation on TIA-1 antigen expression

When peripheral blood T lymphocytes are cultured in Roswell Park Memorial Institute (RPMI) media supplemented with 10% fetal calf serum in the presence or absence of activating stimuli, unstimulated T cells express a 15 kd protein that reacts with TIA-1 on an immunoblot. Cells cultured over an 8 day period in the absence of activation stimuli progressively lose their ability to express the 15 kd protein, while acquiring a 28 kd immunoreactive species. In the presence of phorbal-myristic acetate, the expression of both forms of TIA-1 antigen is decreased. The T cell mitogen, Con A, induces the expression of large amounts of both the 15 kd and the 28 kd immunoreactive forms.

In addition, two higher molecular weight species appear after 6 days in culture with Con A. Antibodies reactive with CD3 similarly induce the expression of these higher molecular weight forms of TIA-1-reactive antigen while phytohemaglutinin tends to diminish expression of TIA-1-reactive antigens. The high molecular weight immunoreactive species appear to be disulfide-linked multimers of the 15 kd monomer. When cell lysates prepared from 6 day Con A activated T cells are separated on SDS-PAGE under reducing conditions, and then subjected to immunoblotting with TIA-1, all of the high molecular weight immunoreactive species are reduced to the 15 kd monomer.

Intracellular localization of TIA-1 antigen

The intracellular location of the TIA-1 antigen was determined by rupturing cells with nitrogen cavitation and fractionating the lysate in a Percoll gradient. A similar analysis of cultured cytolytic T lymphocytes has demonstrated the presence of high density granules that contain the cytolytic effector molecules serine proteases and perforin (Pasternack et al., Nature 322:740, 1986). When a cloned CD8+ cell line (T4T8Cl) possessing cytolytic activity was fractionated in this manner, two peaks of serine protease activity were observed. When the Percoll gradient fractions were examined by immunoblotting for the presence of TIA-1 reactive material, the majority was found in the low density membrane fraction, which also contained serine protease activity. (The low density membrane fraction is believed to contain less mature cytolytic granules, still in the process of forming (Henkart et al., J. Immunol. 139:2398, 1987).)

Upon examination with immunoelectron microscopy, TIA-1 antigen was found to be localized within specific compartments within T4T8Cl cells but not at the cell surface, either in coated pits or along the plasma membrane. No label was apparent within the rough endoplasmic reticulum or the Golgi apparatus. Intense labeling was found within the first post-Golgi compartment; on membranes or endosome-like structures possessing electron lucent cores; around the membranes of electron dense lysosomal granules; and around membranes of small microvesicles contained within small multi-vesiculate bodies. Both the electron lucent endosomes and the electron dense vesicles were labelled on the membrane. Some cytoplasmic vesicles appeared to be in transition from electron lucent to electron dense structures. In all cases, labelling appeared to be associated with compartment membranes only. TIA-1 antigen appears to be a specific marker of developing cytoplasmic granules.

Comparison of TIA-1 antigen with known proteins

In its tissue distribution, subcellular localization and biochemical structure, TIA-1 antigen resembles several known cytolytic effector molecules. Structures such as tumor necrosis factor (TNF) and lymphotoxin (LT) (Krigler et al., Cell 53:45, 1988; Yamamoto et al., J. Immunol. 137:1878, 1986; Schmid et al., Proc. Natl. Acad. Sci. USA 83:1881, 1986) are about the same size as TIA-1 antigen, and could conceivably share its tissue distribution and intracellular localization. However, when the reactivity of TIA-1 was tested with human TNF and lymphotoxin by immunoblotting, neither TNF nor LT were recognized by this antibody. To determine if the TIA-1 antigen might be a previously undescribed serine protease, T4T8Cl lysates were analyzed by the method of Ferguson et al. (J. Exp. Med. 167:528, 1988). While SDS-PAGE of whole cell lysates revealed bands with serine protease activity migrating at around 30 kd, the ³H-diisopropyl phosphofloridate labeled material was not reactive with TIA-1, suggesting that the TIA-1 antigen is not a serine protease.

Isolation and sequence analysis of cDNA clone encoding TIA-1 antigen

Using standard techniques, a λgt11 cDNA library, prepared from RNA isolated from a cytotoxic T cell clone, was subjected to immunoscreening using TIA-1. Three independent clones expressing fusion proteins reactive with TIA-1 were plague purified, and the recombinant cDNAs were subcloned into pSP65 plasmid DNA (Melton et al., Nucl. Acids. Res. 12:7035, 1984) for expansion of the cloned inserts. Insert DNA was excised from the vector, separated on low melt agarose gels, and extracted with phenol. The largest insert (1.5 kb) was labeled with ³²P-dATP by nick translation and used in cross hybridization analysis with the original three isolates. The probe was shown to cross hybridize with each of the independent isolates but not with lambda isolates unreactive with TIA-1. This probe was then used to reprobe the original cDNA library for full length cDNAs. Ten recombinant plagues that hybridized to the ³²P probe were plague purified, and insert DNA was subjected to agarose gel electrophoresis. Seven of these inserts were 1.5 kb in size.

In order to confirm that the cDNA selected by immunoscreening encoded TIA-1 antigen, the full length cDNA was cloned into pSP65 in both orientations. Recombinant plasmids were expanded, linearized with Pst 1 (a restriction enzyme present in the multilinker but absent in the insert DNA), and used as a template in an in vitro transcription reaction with SP6 RNA polymerase according to the method of Melton et al., id. Both sense and antisense transcripts were separated from the DNA template by electrophoresis in low melting point agarose. RNA transcripts were excised, extracted with phenol, and used as templates in in vitro translation reactions with rabbit reticulocyte lysates (Promega). These reactions were carried out in media containing ³⁵S-methionine, and translation products were separated on 12% SDS polyacrylamide gels. (+)strand RNA produced a 15 kd ³⁵S-labeled protein product that was not produced by (−)strand RNA. When this translation product was excised from the gel and run side by side with metabolically labeled TIA-1 antigen immunoprecipitates, these proteins co-migrated.

The 1.5 kd insert described above was subcloned into pSP65 plasmid DNA and used to make a series of 5' unidirectional deletion mutants using exonuclease III (Erase-a-base, Promega). By sequencing overlapping mutants using the Sanger dideoxy method (Sequenase, Promega), the sequence of the cDNA encoding the TIA-1 antigen was obtained (FIGURE). Analysis of this sequence reveals a 191 amino acid open reading frame at the 5' end of the cDNA. If translation begins at the second methionine, which is the first to conform to the consensus eukaryotic initiation sequence (Kozak, Nucleic Acid Research, 12:857, 1984), then the predicted size of the encoded translation product is 16,502 kd. The predicted amino acid sequence also includes six methionines and one cysteine, a result consistent with metabolic labeling experiments. A comparison of this sequence with the Genbank/EMBL DNA database, the translated Genbank, and the NBRF protein database revealed no significant homologies with known sequences. These results suggest that the cDNA isolated by immunoscreening as encoding TIA-1 antigen encodes a previously undescribed component of T lymphocytes.

Use

The monoclonal antibody TIA-1 may be used to identify cytolytic lymphocytes among populations of peripheral blood mononuclear cells, or within tissue sections from pathological specimens. As cytolytic T cells are implicated in the host defense mechanism against invading pathogens, the ability to monitor the presence of cytolytic lymphocytes will provide an early warning of the presence of an infective agent, such as the HIV virus.

An even more sensitive test for cytolytic T cells would use the cDNA or a fragment thereof encoding the TIA-1 antigen as a probe for the presence of nucleic acid encoding the TIA-1 antigen, employing, for example, polymerase chain reaction or in situ hybridization technology.

Deposits

The following deposits have been made with the American Type Culture Collection according to the requirements of the Budapest Treaty:

| Deposit | Date | Accession No. |
|---|---|---|
| E. coli strain T4T8.9-5 | January 5, 1990 | 68202 |
| Hybridoma TIA-1 | January 5, 1990 | HB 10319 |

Applicants' assignee, Dana-Farber Cancer Institute, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

Other embodiments are within the following claims.

We claim:

1. A monoclonal antibody that is immunologically reactive with a protein identical to the 15 kd protein encoded by a plasmid deposited in the ATCC as strain number ATCC 68202.

2. The monoclonal antibody TIA-1 produced by a hybridoma TIA-1 deposited in the ATCC as ATCC number HB 10319, which antibody is specific for the naturally occuring protein encoded by a plasmid deposited in the ATCC as strain number ATCC 68202.

* * * * *

UNITED STATES PATENT AND TRADEMARK OFFICE
CERTIFICATE OF CORRECTION

PATENT NO. : 5,079,343
DATED : January 7, 1992
INVENTOR(S) : Paul J. Anderson, Michel Streuli and Stuart F. Schlossman It is certified that error appears in the above-identified patent and that said Letters Patent is hereby corrected as shown below:

On the title page

In the "References Cited Section", (Anderson et al.), "Cytoplasmi8c" should be --Cytoplasmic.

In the "References Cited Section", (Yamamoto et al.), "TNF-like"" should be --'TNF-like'-- and "vitro,$^1$" should be --Vitro,"--.

Under the "References Cited Section" please add the following --Schmid et al., "DNA Fragmentation: Manifestation of Target Cell Destruction Mediated by Cytotoxic T-Cell Lines, Lymphotoxin-Containing Supernatant," Proc. Natl. Acad. Sci. USA 83:1881-1885 (1986).--

Column 3, line 46, "M CD4$^+$ clone)" should be --M (CD4$^+$ clone)--.

Column 3, line 47, "MM (CD4$^+$ clone" should be --MM (CD4$^+$ clone)--.

Column 5, line 23, "plagues" should be --plaques--.

UNITED STATES PATENT AND TRADEMARK OFFICE
CERTIFICATE OF CORRECTION

PATENT NO. : 5,079,343

DATED : January 7, 1992

INVENTOR(S) : Paul J. Anderson, Michel Streuli and Stuart F. Schlossman

It is certified that error appears in the above-identified patent and that said Letters Patent is hereby corrected as shown below:

Column 5, line 24, "plague" should be --plaque--.

Signed and Sealed this

Twenty-first Day of September, 1993

Attest:

BRUCE LEHMAN

Attesting Officer

Commissioner of Patents and Trademarks